United States Patent
Weber

(10) Patent No.: US 6,488,502 B1
(45) Date of Patent: Dec. 3, 2002

(54) TRANSFER ELEMENT FOR TRANSFERRING THE POSITION OF A DENTAL IMPLANT TO A DENTAL MODEL

(75) Inventor: Heiner Weber, Tuebingen (DE)

(73) Assignee: Friadent GmbH, Mannheim (DE)

( * ) Notice: Subject to any disclaimer, the term of this patent is extended or adjusted under 35 U.S.C. 154(b) by 0 days.

(21) Appl. No.: 09/720,140

(22) PCT Filed: Jun. 22, 1999

(86) PCT No.: PCT/EP99/04329
§ 371 (c)(1),
(2), (4) Date: Apr. 3, 2001

(87) PCT Pub. No.: WO00/00102
PCT Pub. Date: Jan. 6, 2000

(30) Foreign Application Priority Data

Jun. 26, 1998 (DE) .......................... 198 28 479

(51) Int. Cl.[7] ................................ A61C 8/00
(52) U.S. Cl. ........................ 433/173; 433/172
(58) Field of Search ................. 433/172, 173, 433/174, 175, 176

(56) References Cited

U.S. PATENT DOCUMENTS

| | | | |
|---|---|---|---|
| 4,758,161 A | * | 7/1988 | Niznick ...................... 433/173 |
| 5,015,186 A | * | 5/1991 | Detsch ....................... 433/173 |
| 5,106,300 A | * | 4/1992 | Voitik ........................ 433/173 |
| 5,350,297 A | * | 9/1994 | Cohen ........................ 433/173 |
| 5,538,426 A | * | 7/1996 | Harding et al. ............. 433/172 |
| 5,636,989 A | * | 6/1997 | Somborac et al. .......... 433/173 |
| 5,788,494 A | * | 8/1998 | Phimmasone .............. 433/173 |
| 5,938,443 A | * | 8/1999 | Lazzara et al. ............. 433/173 |

FOREIGN PATENT DOCUMENTS

EP 0727193 * 8/1996

* cited by examiner

Primary Examiner—John J. Wilson
(74) Attorney, Agent, or Firm—Crowell & Moring LLP

(57) ABSTRACT

A transfer element for transferring the position of an implanted dental implant body to a master model including at least one element that can be fixed in an impression material for transferring the axial or rotational position of the implant to a dental impression. The invention aims at enhancing the transfer element to enable easy impression making and high precision during transfer of the vertical position of the implant in addition to ensuring anti-rotational blocking. The transfer element includes a core (2) that may be connected to the implant body, and a guide sleeve (4), and the core (2) and the guide sleeve (4) are provided with mutually engaging, corresponding positioning elements (22, 23; 24, 25).

21 Claims, 3 Drawing Sheets

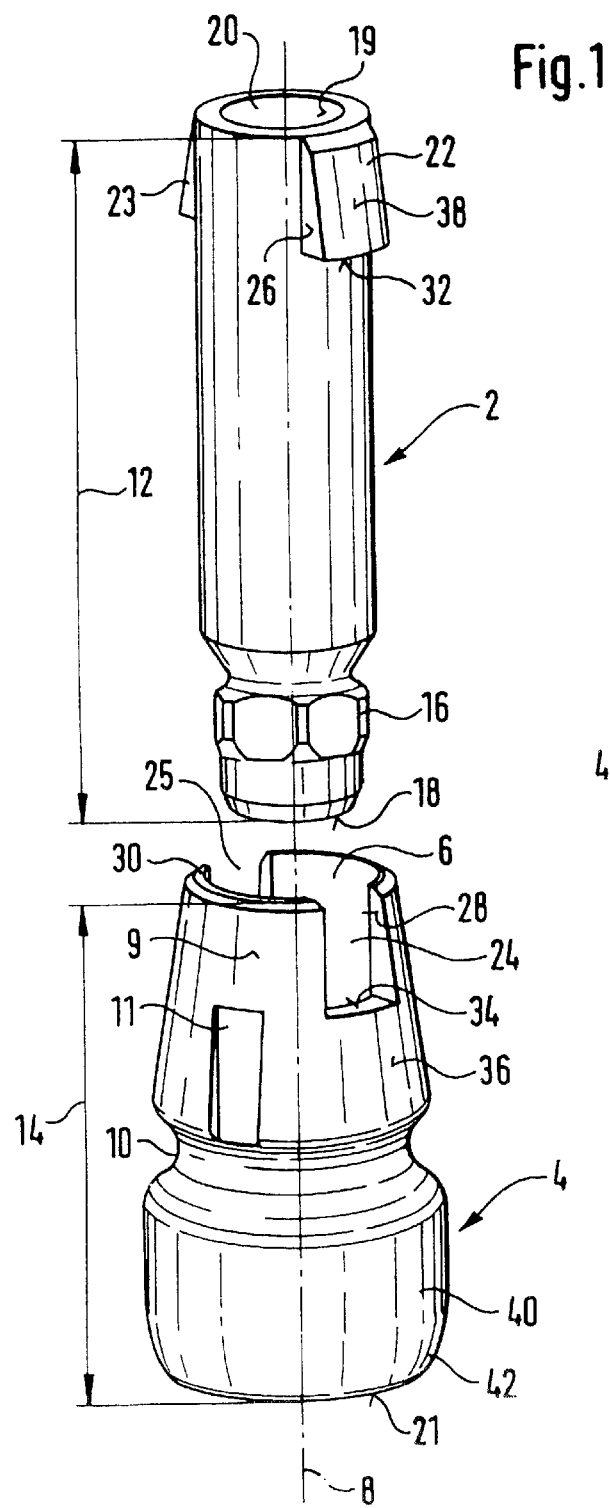
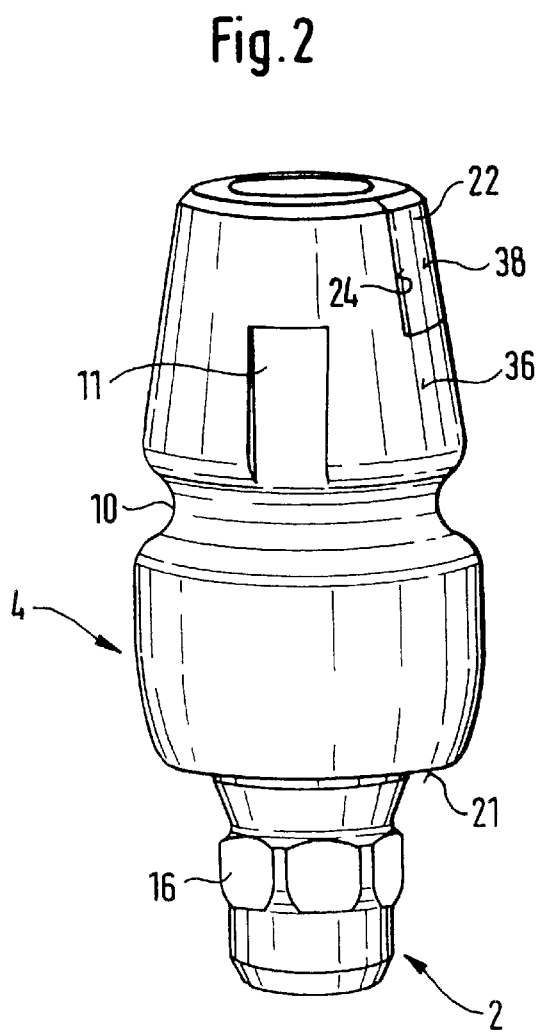

TRANSFER ELEMENT FOR TRANSFERRING THE POSITION OF A DENTAL IMPLANT TO A DENTAL MODEL

BACKGROUND OF THE INVENTION

The invention relates to a dental transfer element.

EP-A-0 727 193 discloses such a transfer element the guide sleeve of which can be connected by means of a core to the implant body previously implanted in the jaw bone. In the area of its coronal end, the implant body has a recess with guide faces aligned axially in parallel in the manner of a hexagon for anti-rotational blocking of a construct that can be connected to the implant body to which a superstructure, a crown or the like, can be fixed. When implant-supported superstructures, crown constructs or the like are created using a master model, a precise transfer of the axial as well as the circular implant position is very important. Corresponding to the hexagonal guide faces, the core is therefore also provided with hexagonally arranged positioning elements formed as outer surfaces aligned in parallel at the end of the core, which engage with the implant body. In other respects the core is essentially arranged within the guide sleeve, which in its area facing the coronal end of the implant body has further positioning elements corresponding to the positioning elements of the core. These further positioning elements are formed as interior hexagonal surfaces. Production of the further positioning elements of the guide sleeve formed as interior surfaces is quite costly. Very close tolerances must be met to permit the transfer of the angular position of rotation of the implant body to a master model by means of the guide sleeve and the impression material. Even slight differences or gaps between the hexagonal interior surface of the guide sleeve and the hexagonal outer surface of the core, which would normally be within tolerance, lead to a significant deviation in the rotational position of the guide sleeve. Despite high-precision production of the interior hexagonal surfaces of the positioning elements of the guide sleeve, transfer errors of the angular position of rotation are difficult to avoid in practice.

WO-A 93/20774 discloses such a transfer element whose core also has positioning elements in the form of hexagonal surfaces, which engage with a hexagon of the implant body. The core, which is capable of axial displacement within the guide sleeve, comprises an axially parallel flattened area, which fits against an axially parallel flattened interior surface of the guide sleeve. In other respects the outer surfaces of the core and the interior surfaces of the guide sleeve fitting against them are cylindrical. In this embodiment, too, the production of said flattened interior surfaces of the guide sleeve is quite costly and even slight deviations due to manufacturing tolerances cause a considerable angle error in the transfer of the angular position.

U.S. Pat. No. 4,758,161 discloses an insert element, which may be connected with the implant body. The insert element comprises a shaft, which may be inserted into an axial recess of the implant body and anchored therein, particularly with dental cement. The insert element further comprises a head for fastening a crown or superstructure. Said head has radial grooves, a constriction and a flattened area for defined localization of the crown or superstructure.

SUMMARY OF THE INVENTION

Based thereon, it is the object of the invention to ensure a simple impression procedure while nevertheless obtaining great precision in the transfer of the angular position. The handling in the dental practice and in the laboratory is also to be improved.

This object is attained by the invention as described and claimed hereinafter.

The transfer element according to the invention is distinguished by its functional construction, serves as a repositioning aid, and ensures with great precision the molding and transfer of the implant position in axial, radial and circumferential direction. The transfer element has two parts comprising on the one hand a core and on the other hand a guide sleeve with mutually corresponding positioning elements for a reciprocal positive-locking, defined fixation in circumferential as well as axial direction. The core is hollow on the inside so that a retaining screw can be guided through it, and it can be axially inserted into the sleeve. The positioning elements, which are advantageously formed as a radial projection and a radial recess, respectively, readily assure an exact mutual alignment. The core has a simple contour and/or geometry and is not costly to produce. The core is partly cylindrical and may be pushed into the sleeve. To take the impression, particularly with an open scoop, the core and the sleeve can be fixed to the implant body implanted into the jaw by means of the retaining screw. When the impression is taken with the open scoop, which is perforated in the implant region, the head of a correspondingly long retaining screw is guided through the perforation. After the scoop is removed, the transfer element remains in the impression and does not need to be repositioned. The core at its one end is advantageously provided with the positioning element and at its diametrically opposite end with the anti-rotational blocking element, particularly in the form of a hexagon, which may be engaged with a corresponding anti-rotational blocking element in the implant body.

The transfer of the circular and axial implant position to the master model by means of the transfer element is thus ensured, and a significantly improved overall accuracy of fit of the superstructure is achieved. The sleeve according to the invention extends up to the gum region and the axial end face fits directly against the axial front face of the implant body, with the end face and front face having substantially the same outside diameter. The axial length of the guide sleeve is at least 50%, particularly at least 65% of the axial core length. On its outer surface the sleeve has at least one constriction, recess, retention element or the like to ensure exact positioning in the impression material. The retention elements to secure the rotational position and/or the axial position in the impression material can advantageously be in the form of flattened areas arranged on the outer surface and produced particularly by milling, or in the form of longitudinal grooves or blind holes or the like. The constriction or recess is advantageously provided approximately in the center of the axial longitudinal extension of the sleeve. The part facing away from the implant body has a substantially cylindrical or approximately conical outer contour, the tip of which is also located on the side facing away from the implant body. The part of the sleeve facing toward the implant body has an outer contour corresponding to the dental construct element in the passage area of the gums and/or the corresponding gum former.

Further developments and specific embodiments of the invention are set forth in the following description.

BRIEF DESCRIPTION OF THE DRAWINGS

The invention will now be described in greater detail, by way of example, with reference to, but not limited to, specific embodiments shown in the drawing in which FIG. 1 is a side elevation of the transfer element in an exploded view, FIG. 2 shows the transfer element in its assembled state of the guide sleeve and core.

DETAILED DESCRIPTION OF PREFERRED EMBODIMENTS

Figure 3:
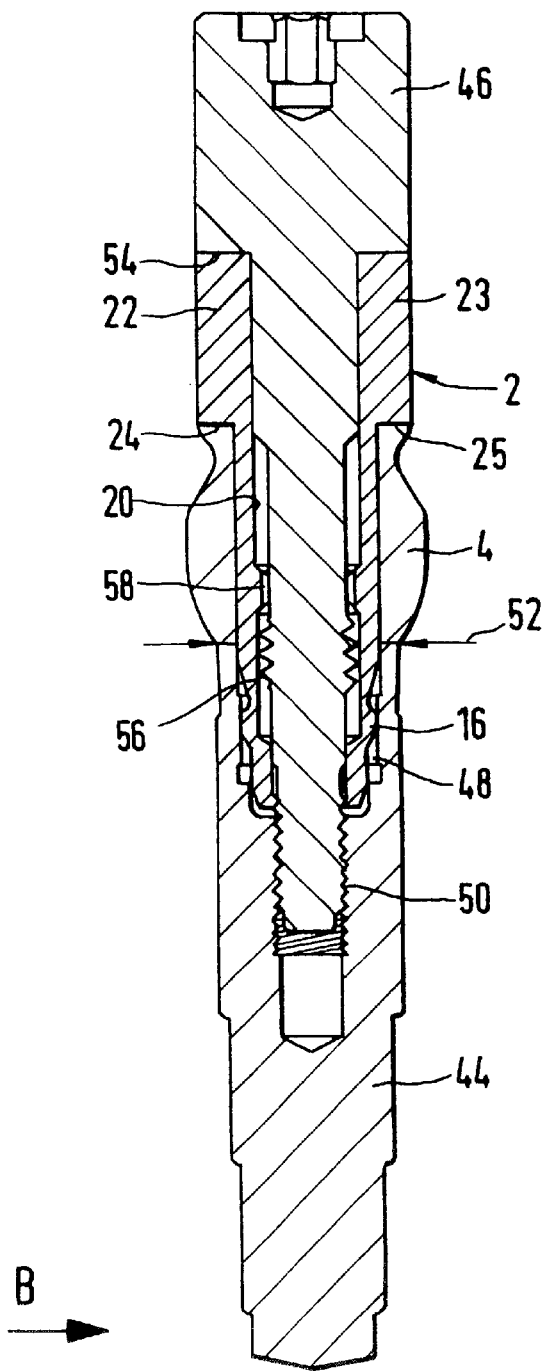
FIG. 3 is an axial longitudinal section through a further embodiment including the implant body and the retaining screw.

The exploded view depicted in FIG. 1 shows the core 2, which comprises an axial through-bore 20 for a retaining screw, as well as the guide sleeve or sleeve 4 with an end-to-end central opening 6. The outside diameter of core 2 is at maximum equal to the diameter of the opening 6 of the sleeve 4, so that the core 2 can be pushed into the sleeve in the direction of the longitudinal axis 8, or the sleeve 4 can be pushed over the core 2, with substantially no radial play. Preferably, the outside diameter of the outer surface of the core 2 and the inside diameter of the inner surface of the sleeve 4 match in such a way that the core can be inserted into sleeve 4 with a sliding fit and then removed therefrom again. In the outer surface 9 of sleeve 4 there is a radial constriction 10 permitting a defined and secure fixation in the impression material. In addition, or as an alternative to the radial constriction 10, sleeve 4, within the scope of the invention, may also have other retention elements, openings or the like for positioning and fixation in the impression material . Preferably, anti-rotational blocking means or retention elements are provided in the area of the outer surface of the sleeve 4, particularly at least one flattened area 11, a longitudinal groove or the like, to ensure a rotationally stable anchoring with in the impression material. The retention elements according to the invention, which form a radially inward pointing indentation or recess in relation to the otherwise substantially rotationally symmetrical outer surface of sleeve 4, ensure axial and radial fixation of the position of the sleeve in the impression material. Thus, they assure a precise transfer of the anti-rotational blocking as well as the axial position from the implant body to the sleeve and the impression material and, ultimately, for the construct, the superstructure or the like.

Core 2 has a length 12, which is greater than length 14 of sleeve 4. Length 14 is advantageously at least half as long as length 12 of the core 2. A specified length 14 of the sleeve 4 of at least 70% of the core length 12 has proven advantageous. At its end facing toward the implant body (not shown) core 2 has an element 16 for anti-rotational blocking or for the transfer of the circular implant position. The anti-rotational blocking element 16 in this case takes the form of a hexagon and may be inserted into a correspondingly shaped recess in the implant body. In the assembled state, the end of core 2 with its blocking element 16 protrudes from sleeve 4.

Instead of element 16 or the hexagon provided on the outer surface 2, other elements may be provided for anti-rotational blocking within the scope of the invention, for example in the area of the front face 18 or in the vicinity thereof in the axially continuous inner surface 19 of the core. It should be noted that, on the inside, core 2 has an axial through-bore 20 permitting the passage of a retaining screw by means of which core 2 and the combined sleeve 4 can be connected for removal with the implant body, which is implanted into the jaw bone. The axial end face 21 of the sleeve 4 fits directly against the opposite front face of the implant body to ensure defined axial alignment.

The core 2 has at least one first positioning element 22, which is associated with a second positioning element 24 of the sleeve 4. The positioning elements are provided in the area of the ends of the core 2 or sleeve 4 facing away from the implant body. As may be seen, the core 2 has preferably two such positioning elements 22, 23 which are diametrically opposite in radial direction. Correspondingly, the sleeve 4 also has two diametrically opposite positioning elements 24, 25. The first positioning element or elements 22, 23 of core 2 are advantageously formed as radial projections of core 2, while the second positioning elements 24 are formed as preferably continuous slots in radially outward direction into which the positioning elements 22, 23 or projections of the core 2 can be inserted for a precise fit. The positioning elements 22, 23 advantageously have axially parallel lateral faces 26 and the second positioning elements 24, 25 of the sleeve 4 have associated lateral faces 28. Preferably, the lateral faces 26 or 28 of core 2 or sleeve 4, respectively, have a snug fit to ensure a defined transfer of the circular implant position. To permit insertion of the first positioning element 22, 23 of core 2, the second positioning element 24, 25 is open toward the end face 30 or the sleeve end. In addition, core 2 and sleeve 4 have mutually associated and corresponding axial support faces 32, 34, so that a defined transfer of the axial position is also ensured.

It is understood that other alignment or fixation means in axial and radial direction of core 2 and sleeve 4 may be specified within the scope of the invention. For example, the first positioning element of core 2 may be constructed as a radial slot for corresponding engagement with a radially inward directed projection of sleeve 4 as the second positioning element. Furthermore, other retention elements, such as gear teeth or gear-like positioning elements, which establish a positive locking connection or positioning of core and sleeve, may be provided.

The previously mentioned radial constriction 10 of sleeve 4 is approximately in the center of the longitudinal extension. The area of sleeve 4 adjacent to constriction 10 and facing away from the implant body preferably has an approximately conical outer contour 36, with the tip of the cone also pointing away from the implant body. The outer surfaces 38 of the radial projections 22, 23 are preferably adapted to the outer contour 36 of sleeve 4. Toward the implant side, sleeve 4 has an initially approximately cylindrical outer contour 40, which adjoins the axial end face 21 via a rounded transition area 42 with a predefined radius.

FIG. 2 shows the transfer element with core 2 and sleeve 4 in its assembled state. The end region of core 2 together with element 16 for anti-rotational blocking projecting beyond the axial end face 21 is clearly visible. The outer surface 38 of the positioning element 22 corresponds to the outer contour 36 of sleeve 4. It can also be readily seen that the two mutually corresponding positioning elements 22, 25, namely the projection and the recess, fit precisely against one another to preclude relative motion in circumferential or axial direction.

FIG. 3 is an axial longitudinal section depicting a further embodiment of the two-part transfer element with core 2 and sleeve 4, including implant body 44 and retaining screw 46. For anti-rotational blocking of a construct or superstructure, the implant body 44, in the area of its coronal end, has preferably internal securing means 48, preferably designed as a hexagon, with which the antirotational blocking element 16 of core 2 engages. At its apical end the retaining screw 46 contains a thread 50, which is screwed into a corresponding female thread of the implant body 44. At its coronal end, the implant body 44 has an outside diameter 52 corresponding to the outside diameter of the adjacent axial end face 21 of sleeve 4. The two positioning elements 22, 23 of the core 2 enter the corresponding elements or recesses 24, 25 of the sleeve 4. Sleeve 4 extends up to the support shoulder 54 of the retaining screw 46, which fixes it in relation to the implant body 44.

According to the invention, the retaining screw 46 comprises a first drive element 56, which is formed, in particular, as a male thread. The axial through-bore 20 of the core 2 comprises a corresponding second drive element 58, which is advantageously formed as a female thread matching the male thread 56 of the retaining screw 46. In the depicted locking position of core 2 and guide sleeve 4 in relation to the implant body 44 to take the impression, the first drive element 56 is advantageously closer to the implant body 44 than the second drive element 58. Advantageously no engagement between the two drive elements 56 and 58 is provided. As will be explained below, after the impression has been taken, as the retaining screw 46 is unscrewed, the core 2 is also readily released in axial direction from the implant body 44 due to the two drive elements 56, 58.

Figure 4:
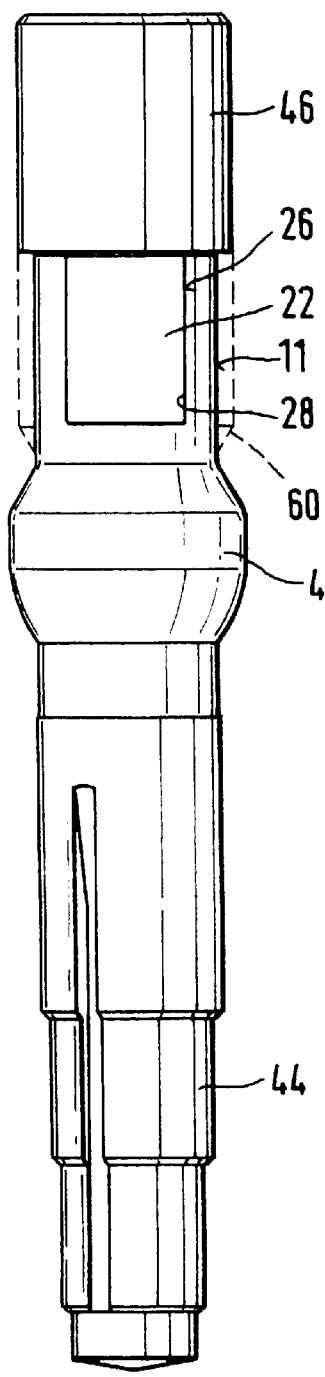
FIG. 4 is a view of the further embodiment according to FIG. 3 in a position rotated by 90° in relation to the longitudinal axis.

FIG. 4 is a side elevation of the transfer element with core 2 and guide sleeve 4 as well as implant body 44 and retaining screw 46 as viewed in direction B according to FIG. 3. Sleeve 4 has two lateral diametrically opposite flattened areas 11, which can be produced very simply, particularly by milling an otherwise substantially cylindrical part, the outer contour of which is indicated by broken lines 60. Sleeve 4 further comprises retention elements 62 into which the impression material penetrates as the impression is being taken, and which thus serve for both rotational and axial blocking of sleeve 4 in the impression material and thus for the transfer of the circular and axial position of the implant body 44.

Figure 5:
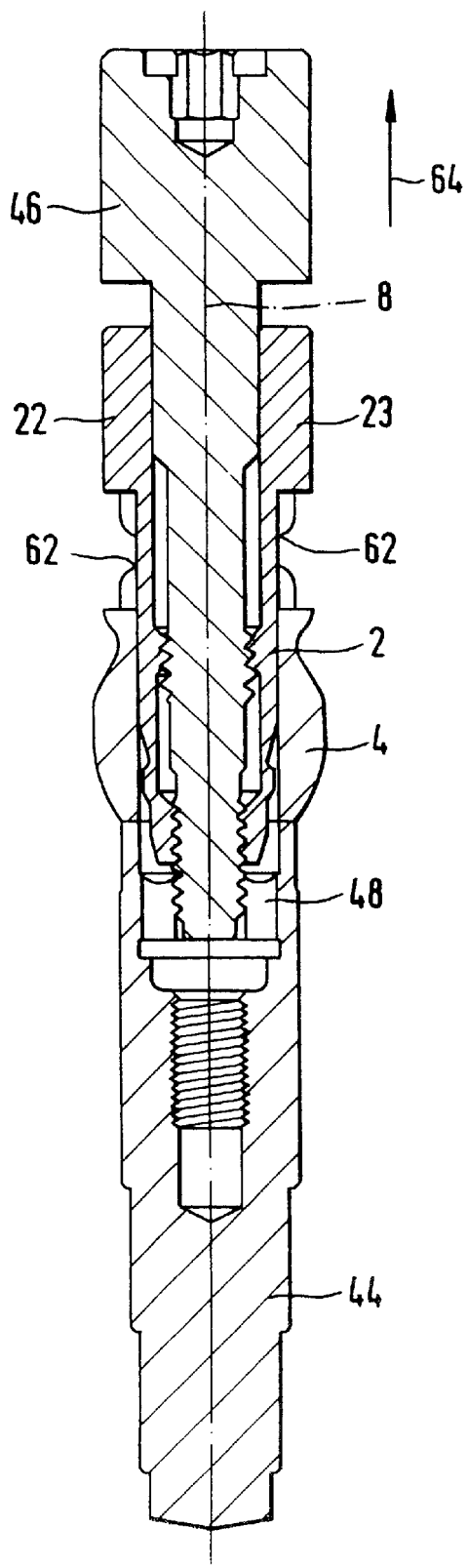
FIG. 5 shows the embodiment according to FIG. 3, with the retaining screw and the core partly detached.

FIG. 5 is an axial longitudinal section in the same plane as FIG. 3, with the retaining screw 46 now being partly unscrewed from the implant body 44 in the direction of arrow 64. As may be seen, the first drive element 56 of the retaining screw 46 and the second drive element 58 of the core 2 are engaged in such a way that when the retaining screw 46 is unscrewed, the core 2 is also already partly released from sleeve 4. This substantially facilitates handling after taking the impression, especially since core 2 can also be readily detached in the direction of longitudinal axis 8 or arrow 64 either simultaneously with or after the complete unscrewing of retaining screw 46. It should be noted that the first positioning elements 22, 23 of the core 2 and the associated positioning elements 24, 25 of the sleeve 4 are matched to one another in such a way that on the one hand anti-rotational blocking is ensured while on the other hand axial release is readily possible based on the aforementioned associated axially parallel lateral faces of core 2 and sleeve 4. The retention elements 62 of guide sleeve 4 are also clearly visible.

Figure 6:
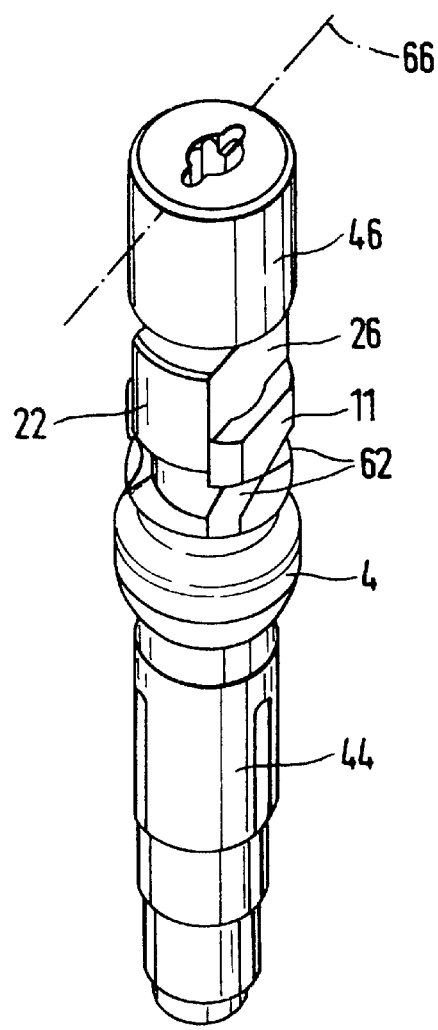
FIG. 6 is a perspective view in accordance with FIG. 5.

FIG. 6 is a perspective view of the core 2, which has been partly detached by means of the retaining screw 46, corresponding to FIG. 5. The section plane in accordance with FIG. 5 is indicated by the broken line 66. The retention elements 62, which are provided in the lateral flattened area 11 of the sleeve 4, are clearly visible.

I claim:

1. A transfer element for transferring the position of an implanted dental implant body to a master model, comprising a guide sleeve to be fixed in an impression material to transfer the axial and rotational position of the implant body, the guide sleeve including two end faces and a central opening extending between the two end faces, one of the end faces abutting the implant body when the guide sleeve is assembled to the implant body, and a core connectable to the implant body, the core being arranged within the central opening and extending at least from one of the end faces to the other end face of the guide sleeve, said core and said guide sleeve being provided with respective mutually corresponding positioning elements, wherein the positioning element of the guide sleeve comprises a radial slot open toward a sleeve end distal to the implant body, and the positioning element of the core comprises a radial projection which engages the radial slot of the guide sleeve.

2. A transfer element according to claim 1, wherein the slot in the guide sleeve has lateral faces parallel to a longitudinal axis of the guide sleeve, and the radial projection on the core has lateral faces which are likewise parallel to the longitudinal axis of the guide sleeve and which fit against the lateral faces of the slot substantially without play.

3. A transfer element according to claim 1, wherein the slot in the guide sleeve extends radially all the way through the guide sleeve.

4. A transfer element according to claim 1, wherein the guide sleeve has a second slot disposed diametrically opposite the first slot, and the core has a corresponding second radial projection which fits into the second slot.

5. A transfer element according to claim 1, wherein the guide sleeve has an axial length which is at least 50% as long as the core.

6. A transfer element according to claim 5, wherein the guide sleeve has an axial length at least 70% as long as the core.

7. A transfer element according to claim 1, wherein the guide sleeve is provided with an external structure for fixing the guide sleeve axially and rotationally in the impression material, said external structure comprising at least one structural feature selected from the group consisting of a radial constriction, a flattened area, a retention element and a recess.

8. A transfer element according to claim 7, wherein said external structure comprises a radial constriction disposed substantially axially centrally in the guide sleeve.

9. A transfer element according to claim 7, wherein said external structure comprises a retention element or a flattened area or a recess disposed in a part of the guide sleeve facing away from the implant body.

10. A transfer element according to claim 7, wherein the guide sleeve comprises a first part facing the implant body which adjoins the implant body via a rounded area, an annular radial constriction adjacent said first part on the opposite side thereof from the implant body, and a further part on the opposite side of said constriction from the implant body, said further part having a conical or cylindrical outer contour, and wherein a flattened area or a retention element or said slot is provided in said further part of the guide sleeve.

11. A transfer element according to claim 10, wherein said first part of the guide sleeve has a substantially cylindrical outer contour.

12. A transfer element according to claim 10, wherein said further part of the guide sleeve has a conical outer contour.

13. A transfer element according to claim 1, wherein the core is provided with anti-rotation elements at an end proximate the implant body.

14. A transfer element according to claim 1, wherein said radial projection is disposed on the core at an end distal to the implant body.

15. A transfer element according to claim 1, wherein the core is substantially cylindrical.

16. A transfer element according to claim 1, further comprising a retaining screw connectable to the implant body, wherein the core is provided with a through-bore for the retaining screw.

17. A transfer element according to claim 16, wherein the retaining screw comprises a first drive element, and the core comprises a corresponding second drive element, such that when the retaining screw is unscrewed, the core is at least partially released from the implant body.

18. A transfer element according to claim 1, wherein the guide sleeve end face, which abuts the implant body, has an outside diameter at least substantially equal to that of the implant body at the point of contact.

19. A transfer element according to claim 1, wherein the core has a proximate end that has a rotation locking element that is configured to engage a corresponding rotation locking element disposed in a borehole of the implant body, wherein when the core is connected to the implant body, the proximate end of the core extends into the borehole of the implant body, and the rotation locking element of the core engages the corresponding rotation locking element of the implant body.

20. A transfer element according to claim 19, wherein when the core is disposed in the guide sleeve and connected to the implant body, the core can be removed from the guide sleeve and the implant body by pulling the core away from the implant through the guide sleeve.

21. A transfer element for transferring the position of an implanted dental implant body to a master model, comprising:

a guide sleeve to be fixed in an impression material to transfer the axial and rotational position of the implant body, a core connectable to the implant body and at least partially arranged within a central opening of the guide sleeve, said core and said guide sleeve being provided with respective mutually corresponding positioning elements, wherein the positioning element of the guide sleeve comprises a radial slot open toward a sleeve end distal to the implant body, and the positioning element of the core comprises a radial projection which engages the radial slot of the guide sleeve, and a retaining screw, wherein the core includes a through-bore for the retaining screw which can be connected with the implant body, wherein the retaining screw comprises a first drive element, and the core comprises a corresponding second drive element, such that when the retaining screw is unscrewed, the core is at least partially released from the implant body, and wherein said first drive element comprises a male thread, and the second drive element comprises a corresponding female thread.

* * * * *